United States Patent
Ecker et al.

(10) Patent No.: US 6,527,897 B1
(45) Date of Patent: Mar. 4, 2003

(54) METHOD AND DEVICE FOR PRODUCING SEGMENTED CONTACT ADHESIVE LAYERS AND FOR APPLYING THE SAME ON A SUBSTRATE

(75) Inventors: Günther Ecker, Neuwied (DE); Bernd Hoffend, Andernach (DE); Fritz Herrmann, Neuwied (DE); Ralf Nittenwilm, Höhr-Grenzhausen (DE)

(73) Assignee: Lohmann GmbH & Co. KG (DE)

( * ) Notice: Subject to any disclaimer, the term of this patent is extended or adjusted under 35 U.S.C. 154(b) by 0 days.

(21) Appl. No.: 09/674,781

(22) PCT Filed: Apr. 19, 1999

(86) PCT No.: PCT/EP99/02612
§ 371 (c)(1),
(2), (4) Date: May 7, 2000

(87) PCT Pub. No.: WO99/56927
PCT Pub. Date: Nov. 11, 1999

(30) Foreign Application Priority Data

May 7, 1998 (DE) .......................... 198 20 366

(51) Int. Cl.[7] .................. B29C 35/08; B29C 65/02; B29C 65/78
(52) U.S. Cl. ............... 156/230; 156/232; 156/272.8; 156/275.5; 156/379.6; 156/542
(58) Field of Search ............... 156/230, 232, 156/272.2, 272.8, 275.5, 289, 379.6, 538, 540, 541, 542

(56) References Cited

U.S. PATENT DOCUMENTS

| 3,623,926 | A | 11/1971 | Sager |
| 4,223,067 | A | 9/1980 | Levens |
| 5,135,686 | A | 8/1992 | Masuhara et al. |
| 5,344,681 | A | 9/1994 | Calhoun et al. |
| 5,569,348 | A | 10/1996 | Hefele |
| 5,569,484 | A | 10/1996 | Muller et al. |
| 5,715,654 | A | 2/1998 | Taylor et al. |
| 6,059,913 | A | 5/2000 | Asmussen et al. |

FOREIGN PATENT DOCUMENTS

| DE | 42 11 448 | 10/1993 |
| DE | 42 30 589 | 2/1994 |
| DE | 195 47 691 | 4/1997 |
| DE | 297 14 146 | 10/1997 |
| EP | 0 347 741 | 12/1989 |
| EP | 0 415 508 | 3/1991 |
| EP | 0 675 183 | 10/1995 |
| EP | 0 748 673 | 12/1996 |

*Primary Examiner*—Michael W. Ball
*Assistant Examiner*—John T. Haran
(74) *Attorney, Agent, or Firm*—D. Peter Hochberg; Katherine R. Vieyra; Sean Mellino

(57) ABSTRACT

The invention relates to a process and a device for manufacturing segmented pressure-sensitive adhesive layers and applying the same to a substrate, involving the use of a reaction medium containing radiation-inducible polymers and/or prepolymers of olefinically unsaturated compounds and the addition of a photoinitiator.

18 Claims, 1 Drawing Sheet

Figure 1:
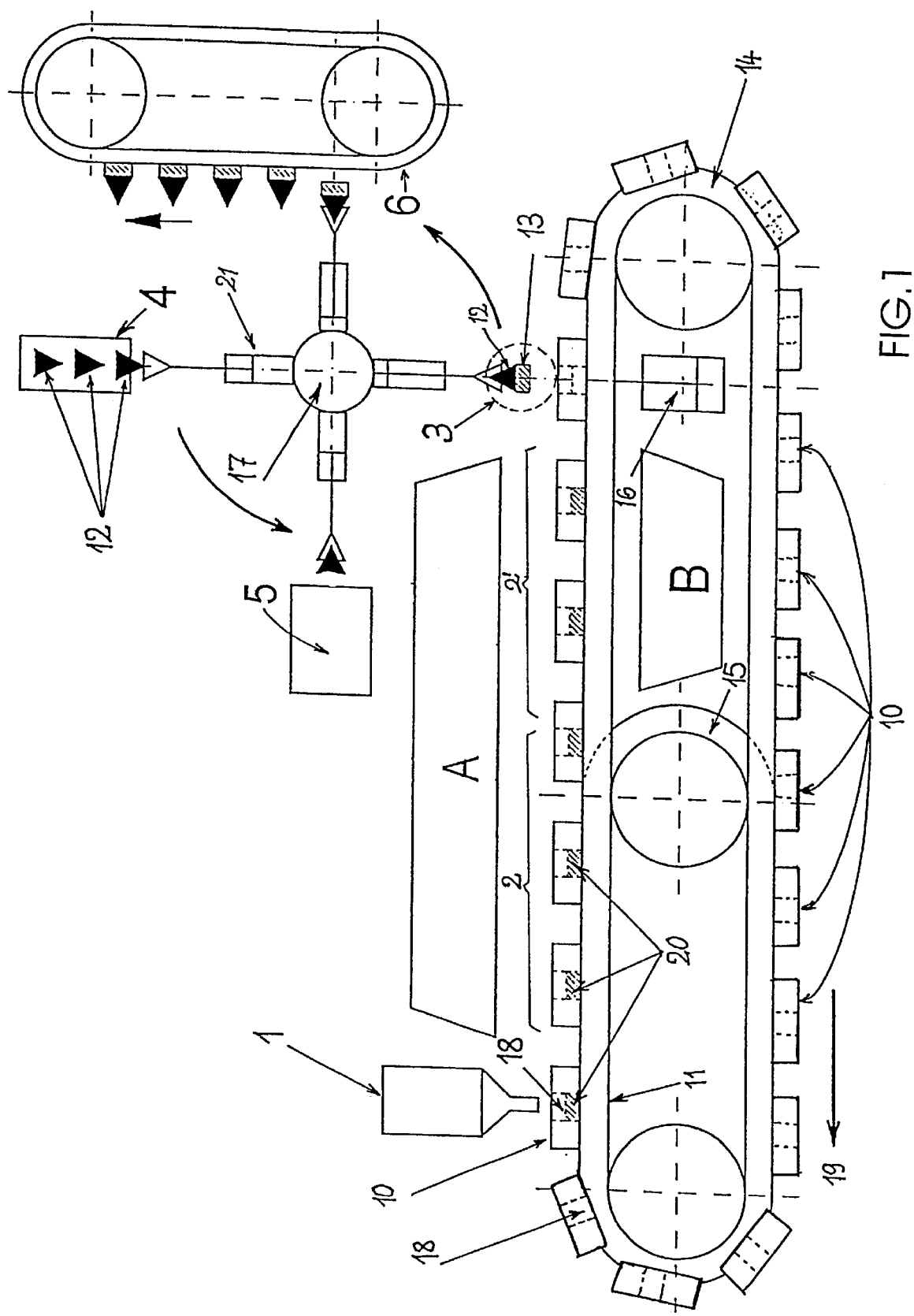

METHOD AND DEVICE FOR PRODUCING SEGMENTED CONTACT ADHESIVE LAYERS AND FOR APPLYING THE SAME ON A SUBSTRATE

BACKGROUND OF THE INVENTION

The invention relates to a process and a device for manufacturing segmented pressure-sensitive adhesive layers and applying the same to a substrate, involving the use of a reaction medium containing radiation-induced monomers and/or prepolymers of olefinically unsaturated compounds, and optionally the addition of a photoinitiator.

DESCRIPTION OF THE PRIOR ART

Segmented pressure-sensitive adhesive layers are widely used in practice, for example, in such pressure-sensitive adhesives which are required to be water- or gas-permeable. Also, in some cases, reducing the consumption of pressure-sensitive adhesive is a reason for the segmentation of a pressure-sensitive adhesive layer.

Furthermore, segmentation is required if small areas are stuck to substrates. Here, it is only the area to be adhered which is to be provided with a segment of the pressure-sensitive adhesive layer.

The processes for segmentation, punching, knife application, and screen printing are known above all. Among these, punching has the disadvantage of entailing large amounts of waste. Knife application only permits production of limited layer thicknesses, which also applies to screen printing. The latter moreover requires a considerable expenditure in terms of the provision of contours.

U.S. Pat. No. 5,344,681 describes a process for segmentation wherein pressure-sensitive adhesive segments are produced in recesses of a carrier material. This involves particular difficulties in connection with the removal of the segments from the recesses.

SUMMARY OF THE INVENTION

Starting from the aforementioned prior art, it is the object of the invention to provide a process and a device which enable the manufacture of segmented pressure-sensitive adhesive layers of any desired thickness and contour in an economical manner as well as in a manner which can be readily realized in technical terms, and which are suitable for mechanization with high output using comparatively uncomplicated devices.

To achieve this object in a process for manufacturing segmented pressure-sensitive adhesive layers and for applying the same to a substrate, using a reaction medium containing radiation-inducible polymers and/or prepolymers of olefinically unsaturated compounds under addition of photoinitiators, the following sequence of operational steps is proposed with the present invention:

that the reaction medium is kept ready in a metering and filling station under absence of oxygen, that the empty templates are conveyed, preferably intermittently one after another, with a lower covering of their segment-defining opening put against the said templates, to a filling station wherein they are filled with a dosable amount of the reaction medium, that the filled templates are passed in continuous conveyance below a UV section, whereby the reaction medium is solidified by means of radiation-induced reaction involving at least partial polymerisation, that after removal of the lower covering, the reaction medium, which is then exposed on the upper side and the bottom side, is, during the further transport between an upper and a lower UV section, fully cured from above and from below by continued radiation-induced polymerisation reaction to form the finished pressure-sensitive adhesive layer, that the template, containing the finished pressure-sensitive adhesive layer, is conveyed to a transfer station wherein the pressure-sensitive adhesive layer is pushed out of the template and is combined with a substrate, that, optionally, the substrate which has been equipped with the pressure-sensitive adhesive layer is conveyed by a conveyor belt to a final-manufacturing station (not shown).

The process is suitable for economically and continuously manufacturing segmented pressure-sensitive adhesive layers of any desired thickness and contour in a manner which is comparatively uncomplicated and can be readily realized in technical terms. More particularly, the process is suitable for use in a fully-mechanized device.

DESCRIPTION OF THE PREFERRED EMBODIMENT

One embodiment of the process provides that the thickness of the segmented pressure-sensitive adhesive layer is defined by the thickness of the template.

Furthermore it is provided by the invention that the template and the lower covering are rendered anti-adhesive, with the template and lower covering being made of dehesive material or the inner walls of the opening and the covering preferably being provided with a dehesive coating.

A further embodiment of the process provides that the polymerization reaction is performed by irradiating the reaction medium with ultraviolet light or electron radiation, and that the ultraviolet light is preferably generated by a laser.

The process is further characterized in that to produce the pressure-sensitive adhesive layer, acrylate-based pressure-sensitive adhesives are selected with preference, and that the mixture of monomers is principally employed under addition of a photoinitiator.

Also, a prepolymer may be used for polymerization. Since during polymerization, the reaction medium is subjected to a volume shrinkage, a corresponding embodiment of the process provides for the addition to the reaction medium of an additive compensating the volume shrinkage occurring in the course of polymerization.

Since the reaction medium must be protected from access of oxygen during its handling up to the time of performing the polymerization reaction, it has proved advantageous to render the environment of the template inert by means of nitrogen, in order to increase the degree of reaction. Since in the case that the reaction medium is metered into an opening of the template it is not absolutely necessary that said opening be filled-up completely, the thickness of the pressure-sensitive adhesive can be adjusted in accordance with the filling amount to be metered, i.e. the thickness can be smaller than the thickness of the template. As a consequence, in the manufacture of the adhesive layer it is possible to vary the thickness within relatively broad limits without the need of making a new template for each thickness.

A device for manufacturing segmented pressure-sensitive adhesive layers and applying the same to a substrate, more particularly for realizing the process according to the invention, is characterized by the following structural features:

a continuous conveyor belt or chain for templates to be conveyed in circulation, a base or support belt running synchronously within the said conveyor belt, under section-wise formation of a lower covering, a first, upper UV section and a subsequent lower UV section, a transfer station comprising a template-emptying device.

As a transfer station, a turnstile is suitable.

In the vertical axis, a turnstile is mounted above the template to be emptied. From below, the contoured adhesive tape is pushed upwards out of the template by means of a plunger or punch. The turnstile consists of 4 arms fitted at a distance of 90°, each arm having a suction foot and a pneumatic cylinder.

A cycle starts at 0° at the magazine (4), from which the suction device takes out the piece which is to be rendered self-adhesive. The arm is rotated through 90° counter-clockwise and reaches a station (5) where the surface is processed (e.g. corona discharge pre-treatment). After a rotation of altogether 180°, at the push-out and transfer station (3) the piece is placed onto the template in exact position. With the aid of the push-out plunger provided at the bottom side, the piece, which has been rendered self-adhesive, is then jointly removed from the template. The said piece, after a further rotation of altogether 270°, is placed on a dehesive conveyor-belt (6) and is subsequently subjected to final manufacturing processes. After the final 90° rotation, the cycle is repeated, respectively, started anew (360°=0°).

The device is comparatively uncomplicated and is suitable for mechanized, continuous production of segmented pressure-sensitive adhesive layers using uncomplicated technological means.

One embodiment of the device provides that the templates have openings to receive the reaction medium, said openings having unrestricted segment-defining geometric shapes.

Furthermore, an embodiment of the device may be characterized in that the base or support belt in parts has segment-shaped protuberances forming pressure-sensitive adhesive-free volume portions by projecting into openings of templates and preventing the filling thereof with reaction medium. These protuberances have been rendered dehesive. They offer the possibility of forming areas which are surrounded on all sides by pressure-sensitive adhesive. Finally, the device provides that the templates have a thickness of between 0.5 to 6 mm.

Further details, features and advantages of the invention will become apparent from the following explanation of an embodiment example which is schematically represented in the drawings. The device shown in the Figure comprises a continuous conveyor belt or chain 14 for templates 10 to be conveyed in circulation. These are attached, at pre-determined distances from each other, to the transport chain 14 and circulate clockwise according to arrow 19 about a respective pair of deflector rolls. Each of the said templates 10 has segment-defining openings 18 which are closed in the region of the filling station 1 at their bottom side by a support belt 15 under formation of a lower covering 11, so that at the filling station 1 the still liquid reaction medium can be filled in portions into each opening 18. The reference numeral 20 designates the filling amount in each template 10. The filling amount may take up only part of the thickness of the template—as illustrated —but it may also from case to case fill up the template 10 in its full height. After a template 10 has been filled with reaction medium at the filling station 1, it runs in continuous transport initially under a UV section A, in a section 2 of the line, and subsequently thereto in a section 2' of the line between an upper UV section A and a lower UV section B, with the reaction medium, which is then exposed at the upper side and the bottom side, being fully cured from above and from below by continued radiation-induced polymerisation reaction to form the finished pressure-sensitive adhesive layer 13.

At the intersection of the transport distances 2 and 2' the support belt 15 had previously run off downwards, thus removing the lower covering 11, and thereby exposed the underside of the reaction medium for polymerization reaction from below.

Then the template 10 containing the finished pressure-sensitive adhesive layer 13 is conveyed to the transfer station 3, where the pressure-sensitive adhesive layer 13 is pushed out from the template 10 with the aid of a plunger- or punch-shaped emptying device 16, and is delivered to the transfer station 3.

In the transfer station 3, with the aid of the template-emptying device 16 the ready-polymerized pressure-sensitive adhesive layer 13 is delivered, after it has been pushed out of the template 10, to an arm of the conveyor means 17 configured as a turnstile, and is held therein, for example, by action of suction.

The turnstile 17 takes individual substrates 12 from a stock (not shown in detail) and delivers them to an arm, each arm being provided with a suction foot and compressed-air cylinder.

A cycle starts at 0° rotation at the magazine or depot 4, from which the suction arm 21 removes the piece 12 which is to be rendered self-adhesive. The arm is then rotated through 90° anti-clockwise and reaches station 5, where the surface of a piece 12 is processed, for example, by coronary pre-treatment. After a further rotation through altogether 180°, at transfer station 3 the piece 12 is placed in exact position on the template 10, whereafter, with the aid of the push-out plunger 16 provided at the bottom side, joint removal of the piece which has been rendered self-adhesive takes place.

Following a further rotation of the turnstile arm of altogether 270°, the said piece 12, together with the pressure-sensitive adhesive layer 13, is placed on a conveyor belt 6 which has been adjusted to be dehesive, and is subsequently subjected to final-manufacturing processes. After the final 90° rotation, the cycle is completed and a new cycle of 360° will be started.

The invention will be illustrated by means of the following examples.

EXAMPLE 1

From 60 parts by weight of 2-ethylhexyl acrylate 30 parts by weight of methyl acrylate 10 parts by weight of acrylic acid 0.01 parts by weight of Irgacure 184 (1-hydroxy-cyclohexyl-phenyl ketone)

an approx. 8% polymer-monomer solution is prepared. At a wavelength of approx. 280 nm, the photoinitiator disintegrates, the reaction is started, which reaction is stopped by switching off the UV lamps when a viscosity of approx. 3 Pa·s has been reached.

Subsequently, 0.6%-wt. of DPGDA (dipropylene glycol diacrylate) and 0.6%-wt. of the photoinitiator Irgacure 1800

(75%-wt. of 1-hydroxy-cyclohexylphenyl ketone and 25%-wt. of Bis(2,6-dimethoxybenzoyl)-2,4,4-trimethylpentyl phosphine oxide) are added to the prepolymer. By adding 2-ethylhexyl acrylate, the viscosity is controlled and the dosable, reactive polymer-monomer mixture is obtained, which is stored under absence of oxygen.

This adhesive was dosed into the cavity of a segment-defining template wherein the letter "L" had been formed. The basic body of the "L" is 6 mm in width, the horizontal and vertical limbs have a length of 20 and 30 mm, respectively. This cavity was milled into a 1.5 mm-thick Teflon plate.

The polymer solution is dosed by means of a piston pump and an aluminium pipe (inner diameter 2 mm) into the cavity between siliconized polyester film and the opening ("L-mold") seated thereon. The mold is filled completely, the volume amounts to 0.35 cm$^3$. The filled template is irradiated for 15 seconds with a UV laser in a chamber 15 which has been rendered inert with nitrogen.

Type: Lextra 200 (by the firm of Lambda Physik, Göttingen), wavelength: 351 nm, impulse rate 5–30 Hz, mean power 10 W, splaying 30 mm×40 mm, whereby the segmented adhesive is polymerized and largely cured. Subsequently, the template is rotated through 180° and again irradiated for 15 seconds from the opposite side, whereby the polyacrylate basic body is fully cured (degree of reaction >99%). With the aid of a negative punch (L-shape having a slip of 0.05 mm) the segmented transparent pressure-sensitive adhesive tape is liberated from the template and placed on a siliconized PETP film. An L piece made of rigid PVC and having the same dimensions is subjected to a corona discharge pre-treatment and stuck to the segmented pressure-sensitive adhesive layer, so that a self-adhesive 1.5 mm-thick element results.

EXAMPLE 2

Free-radical substance polymerization as in Example 1. From 90 parts by weight of 2-ethylhexyl acrylate 10 parts by weight of acrylic acid 0.02 parts by weight of Irgacure 500 an approx. 8% polymer-monomer solution is prepared. A target viscosity of 1.5 Pa·s is adjusted. At a wavelength of approx. 200–280 nm the photoinitiator disintegrates, the reaction is started, which reaction is stopped upon reaching the viscosity of approx. 1.5 Pa·s by switching off the UV lamps.

Subsequently, 0.6% HDDA (hexanediol diacrylate) and 0.8% of the photoinitiator Irgacure 1700 (75%-wt. of 1-hydroxy-2methyl-1-phenyl-propane-1-one and 25% of Bis(2.6-dimethoxy-benzoyl)-2,4,4-trimethylpentyl phosphine oxide) are added to the prepolymer. By adding 1.5%-wt. of micro-hollow glass balls Q-CEL® 300 (U.S. Pat. No. 4,223,067) a filled, dosable and reactive polymer-monomer mixture is obtained, which is stored under absence of oxygen.

The L-template of Example 1 is used. The mold is filled only partly, the volume amounts to 0.24 cm$^3$. The polymer solution is dosed by means of a piston pump and an aluminium pressure pipe (inner diameter 2 mm) into the cavity between siliconized polyester film and the opening seated thereon ("L mold"). The mold is filled up completely, the volume amounts to 0.35 cm$^3$. The filled template is irradiated with a UV lamp for 30 seconds in a chamber which has been rendered inert with nitrogen.

Type: UVA fluorescent lamp TL-K40W/10R with reflector, power 40 W, wavelength 315–400 nm, Philips, whereby the segmented adhesive is polymerized and largely cured. Subsequently, the template is rotated through 180° and again irradiated for 15 seconds from the opposite side, whereby the polyacrylate basic body is fully cured (degree of reaction >99%). With the aid of a negative punch (L shape having a slip of 0.05 mm) the segmented, white adhesive tape is liberated from the template and placed on a siliconized PETP film. An L piece made of rigid PVC and having the same dimensions is subjected to a corona discharge pre-treatment and stuck to a segmented pressure-sensitive adhesive layer, so that a 1.0 mm-thick self-adhesive element is obtained.

Owing to the increase in density during the transformation from monomer to polymer, volume shrinkage occurs and thereby a slight curvature in the upper surface of the segmented pressure-sensitive adhesive layer. This phenomenon can be compensated with small doses of common expansion agents such as baking powder or Expancel 551DU by the firm of Nobel Industries, Sweden.

The process according to the invention and the device provided for performing the same are uncomplicated and useful, and can be realized by economical means. In this respect the invention constitutes an optimum solution to the task presented at the outset.

The invention has been described with particular emphasis on the preferred embodiments, but variations and modifications within the spirit and scope of the invention may occur to those skilled in the art to which the invention pertains.

What is claimed is:

1. A process for manufacturing segmented pressure-sensitive adhesive layers and for applying the same to a substrate comprising:

keeping a reaction medium ready in a metering or filling station under the absence of oxygen, wherein the reaction medium contains radiation-inducible polymers and/or prepolymers of olefinically unsaturated compounds under addition of photoinitiators;

providing templates to a conveyor belt or chain, wherein each template has a top surface, a bottom surface, and a segment-defining opening that extends from the top surface of the template to the bottom surface of the template;

running a support or base belt within said conveyor belt or chain so that the support or base belt provides a lower covering to a bottom of the segment-defining opening of the templates;

conveying the empty templates with a lower covering one after another on the conveyor belt or chain to said metering or filling station wherein the templates are filled with a dosable amount of the reaction medium;

passing the filled templates in continuous conveyance below an upper UV section, whereby the reaction medium is solidified by means of radiation induced reaction involving at least partial polymerization, wherein the volume of the reaction medium shrinks;

removing the lower covering so that the reaction medium is then exposed on an upper side as well as a bottom side;

transporting the filled templates between the upper UV section and a lower UV section so that the uncovered reaction medium is fully cured from above and below by continued radiation-induced polymerization reaction to form the finished pressure-sensitive adhesive layer, wherein the volume of the reaction medium further shrinks; and conveying the templates, containing the finished pressure-sensitive adhesive layers, to a transfer station wherein the pressure-sensitive adhesive layer is pushed out of the template and is combined with a substrate.

2. Process according to claim 1, wherein the substrate combined with the pressure-sensitive adhesive layer is delivered to a turnstile.

3. Process according to claim 2, wherein the substrate, which is equipped with the pressure-sensitive adhesive layer, is conveyed by a conveyor belt to a final manufacturing station.

4. Process according to claim 1, wherein the thickness of the pressure-sensitive adhesive layer is defined by the distance of the top surface of the template from the bottom surface of the template.

5. Process according to claim 1, wherein the template and the lower covering are rendered anti-adhesive.

6. Process according to claim 1, wherein the inner walls of the segment-defining opening of the template and the lower covering are provided with an anti-adhesive coating.

7. Process according to claim 1, wherein the reaction medium is irradiated with ultraviolet light generated by a laser.

8. Process according to claim 1, wherein the pressure-sensitive adhesive layers are acrylate-based pressure-sensitive adhesives.

9. Process according to claim 8, wherein a photoinitiator is added to the reaction mixture comprising acrylate-based pressure-sensitive adhesives.

10. Process according to claim 1, wherein a prepolymer is used for polymerization.

11. Process according to claim 1, wherein an additive is added to the reaction medium, said additive compensates for the volume shrinkage of the reaction medium in the course of the polymerization.

12. Process according to claim 1, wherein the empty templates are conveyed intermittently.

13. A device for manufacturing segmented pressure-sensitive adhesive layers and applying the same to a substrate comprising:

templates having a top surface, a bottom surface, and a segment-defining opening that extends from the top surface of the template to the bottom surface of the template for receiving a reaction medium;

a continuous conveyor belt or chain for templates to be conveyed in circulation;

a support or base belt running synchronously within said conveyor belt or chain for providing a lower covering to a bottom of the segment-defining opening of the templates;

a upper UV section and a lower UV section; and transfer station comprising a template-emptying device.

14. Device according to claim 13, comprising:

conveyor means configured as a turnstile;

a feed station for feeding substrates to the turnstile;

a processing station within the reach of the turnstile; and a second conveyor belt, rendered anti-adhesive, cooperating with the turnstile.

15. Device according to claim 13, wherein said templates have openings to receive the reaction medium, said openings having unlimited, segment-defining geometric shapes.

16. Device according to claim 13, wherein the support or base belt in places has segment-shaped protuberances which form pressure-sensitive adhesive-free volume portions by projecting into the openings of templates and preventing that the same are filled with reaction medium.

17. Device according to claim 13, wherein the protuberances are rendered anti-adhesive.

18. Device according to claim 13, wherein the templates have a thickness of between 0.5 to 6 mm.

* * * * *

UNITED STATES PATENT AND TRADEMARK OFFICE
CERTIFICATE OF CORRECTION

PATENT NO. : 6,527,897 B1
DATED : March 4, 2003
INVENTOR(S) : Gunther Ecker et al.

It is certified that error appears in the above-identified patent and that said Letters Patent is hereby corrected as shown below:

<u>Title page,</u>
Item [86], § 371 (c)(1), (4) Date:, "May 7, 2000" should be -- November 6, 2000 --

Signed and Sealed this

Eighth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,527,897 B1
DATED        : March 4, 2003
INVENTOR(S)  : Gunther Ecker et al.

It is certified that error appears in the above-identified patent and that said Letters Patent is hereby corrected as shown below:

<u>Title page,</u>
Item [86], § 371 (c) (1), (4) Date:, "May 7, 2000" should be -- November 6, 2000 --

Signed and Sealed this

Fifth Day of August, 2003

JAMES E. ROGAN
*Director of the United States Patent and Trademark Office*